United States Patent
Natarajan et al.

(10) Patent No.: US 11,132,615 B2
(45) Date of Patent: Sep. 28, 2021

(54) GENERATING AN EXPECTED PRESCRIPTIONS MODEL USING GRAPHICAL MODELS

(71) Applicant: International Business Machines Corporation, Armonk, NY (US)

(72) Inventors: Ramesh Natarajan, Pleasantville, NY (US); Peder A. Olsen, New York, NY (US); Sholom M. Weiss, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 1266 days.

(21) Appl. No.: 14/643,656

(22) Filed: Mar. 10, 2015

(65) Prior Publication Data
US 2016/0267224 A1    Sep. 15, 2016

(51) Int. Cl.
*G06N 7/00* (2006.01)
*G06Q 10/06* (2012.01)
(Continued)

(52) U.S. Cl.
CPC ............ *G06N 7/005* (2013.01); *G06F 19/00* (2013.01); *G06N 20/00* (2019.01);
(Continued)

(58) Field of Classification Search
None
See application file for complete search history.

(56) References Cited

U.S. PATENT DOCUMENTS 7,813,937 B1   10/2010  Pathria et al.
8,429,113 B2 *  4/2013  Madhok ................. G06Q 10/00
                                              706/52
(Continued)

FOREIGN PATENT DOCUMENTS

WO   WO-2012011997 A1 *  1/2012 ............. G16H 20/10

OTHER PUBLICATIONS

Jafar Adibi, Mining sequential data through layered phases, 2002, ProQuest Publishing Library, pp. 33, 66, 107, 112, 119, 124, 125, 139, 167, 168, 209, 215, 258, 296, and 299, available at https://dialog.proquest.com/professional/docview/305569897?accountid=161862 (last vistited Dec. 4, 2018). (Year: 2002).*

(Continued)

*Primary Examiner* — Elaine Gort
*Assistant Examiner* — Nicholas Akogyeram, II
(74) *Attorney, Agent, or Firm* — William H. Hartwell

(57) ABSTRACT

Software that performs the following steps: (i) receiving data from a first database and data from a second database, (ii) identifying a training subset and a test subset from the received data; (iii) generating a first graphical model using data from the training subset; (iv) generating a second graphical model using data from the training subset; (v) determining respective weights for the first graphical model and the second graphical model by using an expectation maximization method on data from the test subset; (vi) generating a third graphical model by interpolating at least the first graphical model and the second graphical model using their respectively determined weights; and (vii) defining one or more links between the data from the first database and the data from the second database using the third graphical model.

20 Claims, 7 Drawing Sheets

(51) Int. Cl.
G16H 10/60 (2018.01)
G06N 20/00 (2019.01)
G16H 20/10 (2018.01)
G16H 70/40 (2018.01)
G06F 19/00 (2018.01)

(52) U.S. Cl.
CPC ......... *G06Q 10/0635* (2013.01); *G16H 10/60* (2018.01); *G16H 20/10* (2018.01); *G16H 70/40* (2018.01); *Y02A 90/10* (2018.01)

(56) References Cited

U.S. PATENT DOCUMENTS

| | | | | |
|---|---|---|---|---|
| 2008/0133275 | A1* | 6/2008 | Haug | G06Q 10/06 705/3 |
| 2011/0161108 | A1* | 6/2011 | Miller | G06Q 10/10 705/3 |
| 2011/0288886 | A1* | 11/2011 | Whiddon | G06F 19/328 705/3 |
| 2011/0313965 | A1* | 12/2011 | Madhok | G06Q 10/00 706/52 |
| 2013/0085769 | A1 | 4/2013 | Jost et al. | |
| 2014/0257832 | A1 | 9/2014 | Hermiz et al. | |
| 2014/0257846 | A1 | 9/2014 | Hermiz et al. | |
| 2014/0278479 | A1* | 9/2014 | Wang | G06F 19/328 705/2 |
| 2015/0356252 | A1* | 12/2015 | Beker | G06Q 10/10 705/3 |

OTHER PUBLICATIONS

Bolton et al. "Statistical Fraud Detection: A Review". Statistical Science 2002, vol. 17, No. 3. pp. 235-255.
Bolton et al. "Unsupervised Profiling Methods for Fraud Detection". Proc. Credit Scoring and Credit Control VII. 2001. <http://citeseerx.ist.psu.edu/viewdoc/summary?doi=10.1.1.24.5743&rank=1>.
Cooper et al. "Bayesian Biosurveillance of Disease Outbreaks". UAI 2004. pp. 94-103.
Dempster et al. "Maximum Likelihood from Incomplete Data via the EM Algorithm". Journal of the Royal Statistical Society, Series B (Methodological), vol. 39, No. 1. (1977) pp. 1-38.
Forney, G. "The Viterbi Algorithm". Proceedings of The IEEE, vol. 61, No. 3. Mar. 1973.
Katz, S. "Estimation of Probabilities from Sparse Data for the Language Model Component of a Speech Recognizer". IEEE Transactions on Acoustics, Speech, and Signal Processing. vol. ASSP-35, No. 3, Mar. 1987. pp. 400-401.
Kneser, et al. "Improved Backing-off for M-Gram Language Modeling". Copyright IEEE 1995. pp. 181-184.
Koller et al. "Probabilistic Graphical Models". The MIT Press, 2009. Cambridge, MA. England.
Lucas et al. "Bayesian networks in biomedicine and health-care". Artificial Intelligence in Medicine 30 (2004). pp. 201-214. Elsevier. B.V.

Meloni et al. "Improved Learning of Bayesian Networks in Biomedicine". 2009 Ninth International Conference on Intelligent Systems Design and Applications. Copyright 2009 IEEE. pp. 624-628.
Olsen et al. Grace Period Disclosure. "Graphical Models for Identifying Fraud and Waste in Healthcare Claims". Copyright SIAM. pp. 569-577. Downloaded Feb. 6, 2015. <http:www.siam.org/journals/ojsa.php>.
Rabiner et al. "Fundamentals of Speech Recognition". Copyright 1993 AT&T. Englewood Cliffs, New Jersey.
Spiegelhalter, D. "Probabilistic Expert Systems in Medicine: Practical Issues in Handling Uncertainty". Institute of Mathematical Statistics in collaborating with JSTOR to digitize, preserve, and extend access to Statistical Science. Statistical Science 1987 vol. 2, No. 1, 3-44. pp. 25-30.
Verduijn, et al. "Prognostic Bayesian networks I: Rationale, learning procedure, and clinical use". Journal of Biomedical Information 40 (2007) pp. 609-618.
Viterbi, A. "Error Bounds for Convolutional Codes and an Asymptotically Optimum Decoding Algorithm". IEEE Transactions on Information Theory, vol. IT-13, No. 2. Apr. 1967. pp. 260-269.
Wainwright et al. "Graphical Models, Exponential Families, and Variational Inference". Foundations and Trends® in Machine Learning. vol. 1, Nos. 1-2 (2008) 1-305.
Wilkinson, D. "Bayesian methods in bioinformatics and computational systems biology". Briefings in Bioinformatics, vol. 8, No. 2. pp. 109-116. Copyright 2007 Oxford University Press.
Allcott; "Social norms and energy conservation"; Elsevier; Journal of Public Economics; 95, (2011);1082-1095; Available online Mar. 21, 2011; © 2011 Elsevier B.V.
Bahl et al.; "A Measure of the Diffculty of Speech Recognition Tasks"; 94th Meeting of the Acoustic Society of America; 62:S63; Suppl. No. 1; 1977.
Donkers et al; "Belief Networks for Bioinformatics"; Studies in Computational Intelligence (SCI), vol. 94; pp. 75-111; 2008; © Springer-Verlag Berlin Heidelberg, 2008.
Huang et al.; "Spoken Language Processing: A Guide to Theory, Algorithm, and System Development"; Prentice Hall PTR; Upper Saddle River, NJ 07458; Microsoft Research; © 2001 by Prentice Hall; pp. 387-389.
Iyengar et al.; "Computer-aided auditing of prescription drug claims"; Springer; Health Care Manag Sci; 2014; Published online: Jul. 3, 2013; vol. 17; pp. 203-214; © Springer Science+Business Media, New York, 2013.
Jelinek; "The Speech Recognition Problem"; Chapter 1; pp. 1-14; in (ed) Statistical Methods for Speech Recognition; The MIT Press; © 1997 Massachusetts Institute of Technology.
Jensen et al.; "Causal and Bayesian Networks"; Chapter 2; pp. 23-50; in (ed): Bayesian Networks and Decision Graphs; Springer; © 2007, Springer Science+ Business Media; Feb. 8, 2007.
Jensen et al.; "Parameter Estimation"; Chapter 6; pp. 195-228; in (ed):Bayesian Networks and Decision Graphs; Springer; © 2007, Springer Science+ Business Media; Feb. 8, 2007.
Pearl; "Introduction to Probabilities, Graphs, and Causal Models"; Chapter 1; pp. 25-38; in (ed): Causality: Models, Reasoning, and Inference; Cambridge University Press; © Judea Pearl, 2000.

* cited by examiner

400

> From: Prescription Fraud Auditor
> To: doctor@ABCHospital.com
> Subject: Your Prescription Scorecard (CONFIDENTIAL)
>
> Dear Doctor,
>
> Please find your prescription scorecard below. — 402
>
> | Drug Prescribed | Prescription Likelihood Score | Outlier? |
> |---|---|---|
> | Painkiller A | 97% | N |
> | Painkiller B | 43% | Y |
> | Painkiller C | 75% | N |
>
> As you can see, Prescription B has been flagged as a potential outlier, based on your previous prescription history and the history of your peers.
>
> Thank You for using our service.
>
> John Doe
> Prescription Fraud Auditor
>
> OS 

FIG. 4

GENERATING AN EXPECTED PRESCRIPTIONS MODEL USING GRAPHICAL MODELS

STATEMENT ON PRIOR DISCLOSURES BY AN INVENTOR

The following disclosure(s) are submitted under 35 U.S.C. 102(b)(1)(A) as prior disclosures by, or on behalf of, a sole inventor of the present application or a joint inventor of the present application:

(i) "Graphical Models for Identifying Fraud and Waste in Healthcare Claims", Peder A. Olsen, Ramesh Natarajan, and Sholom M. Weiss, SIAM International Conference on DATA MINING, Philadelphia, Pa., April 2014.

BACKGROUND OF THE INVENTION

The present invention relates generally to the field of healthcare, and more particularly to detecting fraud and/or abuse in medical treatment activity.

Health care (or "healthcare") is widely and generally known as the diagnosis, treatment, and prevention of physical and mental impairments in human beings. Likewise, health insurance (or "healthcare insurance") is insurance against the risk of incurring healthcare expenses. Typically, the cost (to the insured) of health insurance is associated with the overall risk of healthcare expenses for the insured. An important factor known to lead to increases in healthcare expenses (and therefore health insurance costs) is fraud and abuse in medical treatment activity. For example, fraudulent health insurance claims for medically unnecessary medical procedures and/or prescriptions increase the cost of covering healthcare expenses and therefore can lead to an increase in health insurance premiums (as well as significant health damages to those receiving the medically unnecessary medical procedures and/or prescriptions). As such, fraud and abuse detection is an important focus in the healthcare industry.

Graphical models are known. A graphical model is a probabilistic model for which a graph demonstrates a conditional independence structure between variables. Generally speaking, graphical models use a graph-based representation as the basis for encoding a complete probability distribution over a multi-dimensional space. Known types of graphical models include, for example, Bayesian networks and Markov networks. Graphical models can be used in combination with sets of data to identify predictive relationships between variables. Some sets, called "training sets," are used to discover potentially predictive relationships, while other sets, called "test sets" are used to assess the strength and/or utility of those potentially predictive relationships.

Dynamic programming is known. Dynamic programming is a method for solving complex problems by breaking them down into collections of simpler subproblems. Generally speaking, dynamic programming algorithms examine previously-solved subproblems and combine their solutions to give the best solution to a given problem. One known dynamic programming algorithm, which finds the most likely sequence of hidden states that result in a sequence of observed events, is called the Viterbi algorithm.

SUMMARY

According to an aspect of the present invention, there is a method, computer program product and/or system that performs the following steps (not necessarily in the following order): (i) receiving, by one or more computer processors, a first set of observed data including data from a first database and data from a second database, the first database and the second database being independent databases that do not directly reference each other, (ii) identifying, by one or more computer processors, from the first set of observed data, a training subset and a test subset, the training subset and the test subset each including data from both the first database and the second database; (iii) generating, by one or more computer processors, a first graphical model using data from the training subset, the first graphical model representing probabilities of receiving certain values of a first variable of the first database in combination with certain values of a second variable of the second database; (iv) generating, by one or more computer processors, a second graphical model using data from the training subset, the second graphical model representing probabilities of receiving certain value of the first variable of the first database in combination with certain values of a third variable of the second database; (v) determining, by one or more computer processors, respective weights for the first graphical model and the second graphical model by using an expectation maximization method on the data from the test subset; (vi) generating, by one or more computer processors, a third graphical model by interpolating at least the first graphical model and the second graphical model using the respectively determined weights for the first graphical model and the second graphical model; and (vii) defining, by one or more computer processors, one or more links between the data from the first database and the data from the second database using the third graphical model.

BRIEF DESCRIPTION OF THE DRAWINGS

FIG. 4 is a screenshot view generated by the first embodiment system;

DETAILED DESCRIPTION

Figure 1:
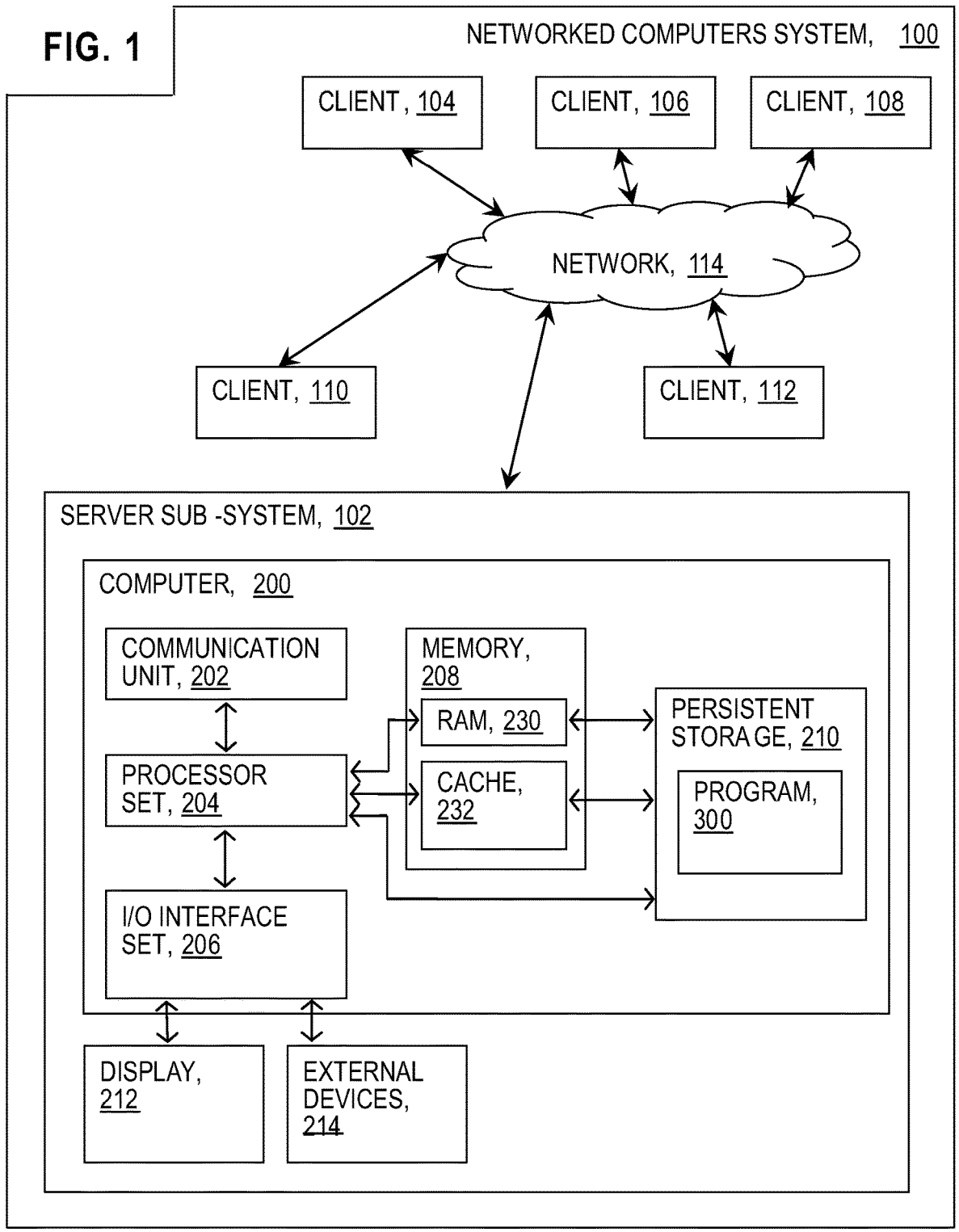
FIG. 1 is a block diagram view of a first embodiment of a system according to the present invention.

An important area of focus in the healthcare (and health insurance) industry is the detection and prevention of fraud and/or abuse in the treatment of medical conditions. Embodiments of the present invention detect potential fraud and/or abuse by creating a predictive model for medical treatments based on existing medical treatment data. More specifically, embodiments of the present invention generate a graphical model with latent variables and test a healthcare provider's prescription data against the generated model using a dynamic programming approach. As a result, prescription scores—indicating the probability that a given prescription should actually occur under the generated graphical model—are generated. This Detailed Description section is divided into the following sub-sections: (i) The Hardware and Software Environment; (ii) Example Embodiment; (iii) Further Comments and/or Embodiments; and (iv) Definitions.

I. THE HARDWARE AND SOFTWARE ENVIRONMENT

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

An embodiment of a possible hardware and software environment for software and/or methods according to the present invention will now be described in detail with reference to the Figures. FIG. 1 is a functional block diagram illustrating various portions of networked computers system 100, including: sub-system 102; client sub-systems 104, 106, 108, 110, 112; communication network 114; computer 200; communication unit 202; processor set 204; input/output (I/O) interface set 206; memory device 208; persistent storage device 210; display device 212; external device set 214; random access memory (RAM) devices 230; cache memory device 232; and program 300.

Sub-system 102 is, in many respects, representative of the various computer sub-system(s) in the present invention. Accordingly, several portions of sub-system 102 will now be discussed in the following paragraphs.

Sub-system 102 may be a laptop computer, tablet computer, netbook computer, personal computer (PC), a desktop computer, a personal digital assistant (PDA), a smart phone, or any programmable electronic device capable of communicating with the client sub-systems via network 114. Program 300 is a collection of machine readable instructions and/or data that is used to create, manage and control certain software functions that will be discussed in detail, below, in the Example Embodiment sub-section of this Detailed Description section.

Sub-system 102 is capable of communicating with other computer sub-systems via network 114. Network 114 can be, for example, a local area network (LAN), a wide area network (WAN) such as the Internet, or a combination of the two, and can include wired, wireless, or fiber optic connections. In general, network 114 can be any combination of connections and protocols that will support communications between server and client sub-systems.

Sub-system 102 is shown as a block diagram with many double arrows. These double arrows (no separate reference numerals) represent a communications fabric, which provides communications between various components of sub-system 102. This communications fabric can be implemented with any architecture designed for passing data and/or control information between processors (such as microprocessors, communications and network processors, etc.), system memory, peripheral devices, and any other hardware components within a system. For example, the communications fabric can be implemented, at least in part, with one or more buses.

Memory 208 and persistent storage 210 are computer-readable storage media. In general, memory 208 can include any suitable volatile or non-volatile computer-readable storage media. It is further noted that, now and/or in the near future: (i) external device(s) 214 may be able to supply, some or all, memory for sub-system 102; and/or (ii) devices external to sub-system 102 may be able to provide memory for sub-system 102.

Program 300 is stored in persistent storage 210 for access and/or execution by one or more of the respective computer processors 204, usually through one or more memories of memory 208. Persistent storage 210: (i) is at least more persistent than a signal in transit; (ii) stores the program (including its soft logic and/or data), on a tangible medium (such as magnetic or optical domains); and (iii) is substantially less persistent than permanent storage. Alternatively, data storage may be more persistent and/or permanent than the type of storage provided by persistent storage 210.

Program 300 may include both machine readable and performable instructions and/or substantive data (that is, the type of data stored in a database). In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer-readable storage media that is capable of storing program instructions or digital information.

The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communications unit 202, in these examples, provides for communications with other data processing systems or devices external to sub-system 102. In these examples, communications unit 202 includes one or more network interface cards. Communications unit 202 may provide communications through the use of either or both physical and wireless communications links. Any software modules discussed herein may be downloaded to a persistent storage device (such as persistent storage device 210) through a communications unit (such as communications unit 202).

I/O interface set 206 allows for input and output of data with other devices that may be connected locally in data communication with server computer 200. For example, I/O interface set 206 provides a connection to external device set 214. External device set 214 will typically include devices such as a keyboard, keypad, a touch screen, and/or some other suitable input device. External device set 214 can also include portable computer-readable storage media such as, for example, thumb drives, portable optical or magnetic disks, and memory cards. Software and data used to practice embodiments of the present invention, for example, program 300, can be stored on such portable computer-readable storage media. In these embodiments the relevant software may (or may not) be loaded, in whole or in part, onto persistent storage device 210 via I/O interface set 206. I/O interface set 206 also connects in data communication with display device 212.

Display device 212 provides a mechanism to display data to a user and may be, for example, a computer monitor or a smart phone display screen.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

II. EXAMPLE EMBODIMENT

Figure 2:
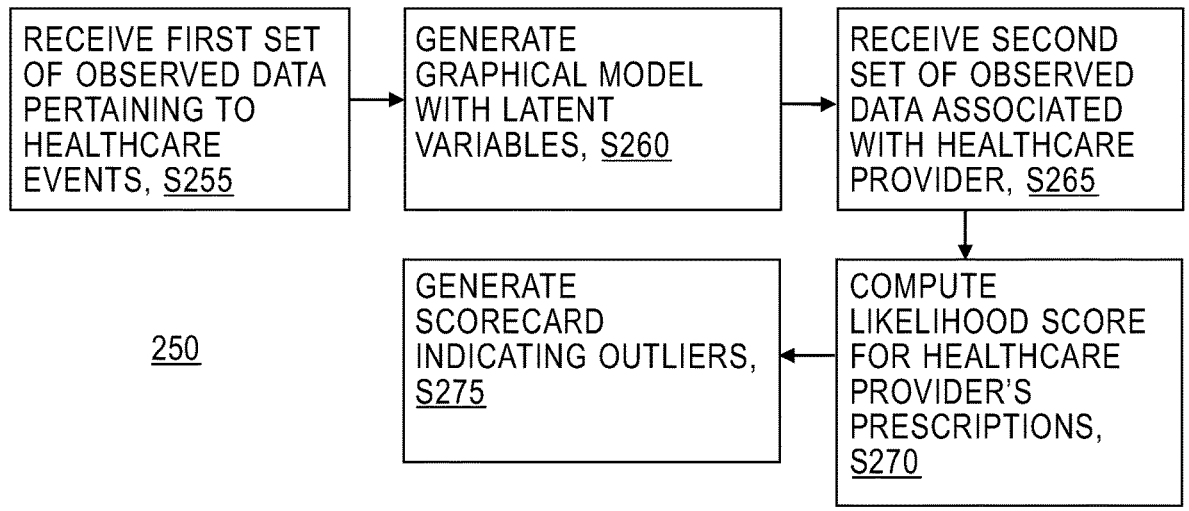
FIG. 2 is a flowchart showing a first embodiment method performed, at least in part, by the first embodiment system.
Figure 3:
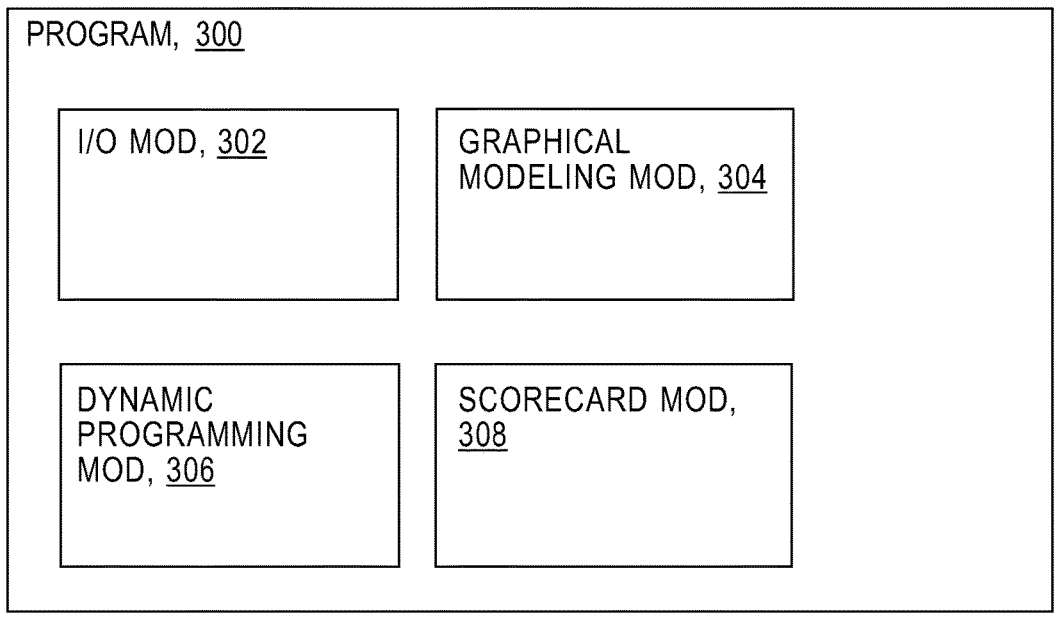
FIG. 3 is a block diagram showing a machine logic (for example, software) portion of the first embodiment system.

FIG. 2 shows flowchart 250 depicting a method according to the present invention. FIG. 3 shows program 300 for performing at least some of the method steps of flowchart 250. This method and associated software will now be discussed, over the course of the following paragraphs, with extensive reference to FIG. 2 (for the method step blocks) and FIG. 3 (for the software blocks).

The following paragraphs refer extensively to an example embodiment according to the present invention. As used herein in this sub-section, any discussion of the "present embodiment," the "example embodiment," the "present example," or the like is meant to refer to this first example embodiment (as opposed to a second example embodiment discussed in the Further Comments and/or Embodiments sub-section of this Detailed Description). Generally speaking, a purpose of the method discussed below is to generate a model for prescription activity and use that model to detect outlier behavior in the prescription activity of a specific healthcare provider (or providers).

Processing begins at step S255, where I/O module ("mod") 302 receives a first set of observed data pertaining to healthcare events. The first set of observed data includes a subset of patient care event data (pertaining to patient care events) and a subset of prescription data (pertaining to prescription events). Patient care event data (also referred to as "medical claims" data in a "medical claims database") may include, for example, data related to doctor visits, hospital visits, medical diagnoses, and/or medical procedures. In fact, patient care event data may relate to any healthcare-related event that is not directly related to prescription activity. Similarly, the prescription data (also referred to as "prescription claims" data in a "prescription database") may include any data related to prescription activity, including, but not limited to the writing, entering, transmitting, and/or filling of a prescription. In the present example embodiment, patient care event data includes data on medical diagnoses, and the prescription data includes data on issued prescriptions for prescription drugs.

In many embodiments of the present invention, the patient care event data and the prescription data originate from differing sources. For example, in some embodiments (such as the second example embodiment discussed in the following sub-section), the patient care event data is received from a medical claims database (for example, from a medical insurance provider), and the prescription data is received from a prescription database (for example, from a prescription drug plan provider). However, this is not necessarily required, and in some embodiments the patient care event data and the prescription data are received from the same database originating from the same source. In the present example embodiment, the medical diagnosis data (that is, the patient care event data) and the prescription data are each received from separate databases that are maintained by the same source, a medical insurance provider.

Processing proceeds to step S260, where graphical modeling mod 304 generates a graphical model representing a probabilistic relationship between the patient care event data and the prescription data. As mentioned previously in the Background section, a graphical model is a probabilistic model for which a graph demonstrates a conditional dependence structure between variables. In many embodiments (including the present example embodiment), the graphical model of the present invention is adapted to represent the probabilistic relationship between the patient care event data and the prescription data such that if given a set of patient care data, the graphical model could assign a probable prescription outcome for that data. The graphical model can be depicted in a number of ways; for example, the graphical model can be depicted as an equation, a graph, or as both an equation and a graph. However, this is not meant to be limiting, and the graphical model can be depicted in any way known (or yet to be known) in the relevant art. For a detailed discussion of graphical models as used in the present invention, see the Further Comments and/or Embodiments sub-section of this Detailed Description.

It should be noted that in the present example embodiment (and in many embodiments of the present invention), the patient care event data and the prescription data are not directly linked (that is, the corresponding databases do not reference each other—the diagnosis data does not include information about prescriptions resulting from a particular diagnosis, and the prescription data does not include information about the diagnoses resulting in a particular prescription). As such, the graphical model includes a set of latent variable(s) representing the values not included in the observed data. In many embodiments (including the present example embodiment), the latent variable(s) are estimated from the first set of observed data using an expectation maximization (or "EM") method. Generally speaking, EM methods (or algorithms) are methods for finding maximum likelihood estimates of parameters in statistical models that depend on unobserved latent variables. For a detailed discussion of the use of EM in the present invention, see the Further Comments and/or Embodiments sub-section of this Detailed Description.

Processing proceeds to step S265, where I/O mod 302 receives a second set of observed data pertaining to healthcare events (sometimes also referred to as the "second set"), where the second set of observed data is associated with a specific healthcare provider. A healthcare provider may be any individual, entity, or group of individuals and/or entities responsible for creating, writing, entering, transmitting, filling, and/or prescribing a prescription. For example, in many embodiments, including the present example embodiment, the healthcare provider is a physician (or doctor) who prescribes prescriptions. In these embodiments, the second set of observed data may include—in addition to data pertaining to specific prescriptions the physician has participated in—any available data pertaining to the physician's past medical diagnoses, procedures the physician has performed/ordered, and/or the physician's treatment history (either for a specific patient or for all patients). In other embodiments, the healthcare provider may by a nurse practitioner, a Physician Assistant, a dentist, a psychologist, or other prescribing individual or entity. In still other embodiments, the healthcare provider may be a pharmacist, a pharmacy technician, or a pharmacy responsible for filling prescriptions.

Processing proceeds to step S270, where dynamic programming mod 306 uses a dynamic programming approach to compute a prescription score for the healthcare provider. Generally speaking, dynamic programming approaches include computer-implemented methods that examine previously solved subproblems and combine their solutions to give the best solution to a given problem. In the present invention, many known (or yet to be known) dynamic programming approaches may be used. For example, in many embodiments, a Viterbi algorithm is used. For a detailed discussion of dynamic programming (and the use of the Viterbi algorithm), see the Further Comments and/or Embodiments sub-section of this Detailed Description.

The prescription score relates to (and in many cases, is based, at least in part, on) a computed probability under the generated graphical model of at least one prescription event of the second set of observed data. Or, stated another way, the prescription score (sometimes also referred to as a "prescription likelihood score") is a measure of how likely, or probable, a particular prescription event (or set of prescription events) is under the graphical model generated in step S260. For example, in one embodiment, if a prescription event from the second set has a high probability under the graphical model, its prescription score is high. If, however, the graphical model determines that the prescription event is not very probable, the prescription score is low—an indicator that fraud and/or abuse may have occurred. Alternatively, in some embodiments, including the present example embodiment, the opposite is true: high probabilities under the graphical model are represented by prescription scores that are close to zero, while low probabilities are represented by larger numbers.

Processing proceeds to step S275, where scoring mod 308 generates a scorecard for the healthcare professional based, at least in part, on the results of step S270. In many embodiments (including the present example embodiment), the scorecard is delivered to the healthcare provider (via I/O mod 302) for the purpose of informing him/her of outlier prescriptions (for example, by flagging prescriptions scores that are below a prescription likelihood threshold). In these cases, the scorecard may be able to positively affect the healthcare provider's prescription actions moving forward (acting as "behavior modification feedback"). In other embodiments, the scorecard is delivered to a third party, such as an auditor, for the purpose of identifying circumstances that may require further investigation. For example, in some situations, the scorecard and the prescription scores may indicate situations where fraud and/or abuse have occurred, either from the healthcare provider, the patient, or someone else involved in the medical treatment process. In these situations, further investigation may be necessary. In other situations, however, no fraud or abuse is present, and the scorecard simply informs the healthcare provider and/or the third party of helpful outlier information.

Example screenshot 400, showing scorecard 402 according to the present embodiment, is shown in FIG. 4. In this example, scorecard 402 is provided in the form of an electronic mail message, where the healthcare provider ("Doctor") is presented with a list of prescription drugs ("Painkiller A", "Painkiller B", and "Painkiller C"). For each prescription drug, the scorecard shows: (i) the actual number of prescriptions; (ii) the expected number of prescriptions; and (iii) an indicator as to whether the prescription activity for that prescription drug is flagged as an outlier (based on the prescription score). As shown in FIG. 4: (i) for Painkiller A, which is not flagged as an outlier, the actual number of prescriptions is 3 and the expected number of prescriptions is 3; (ii) for Painkiller B, which is flagged as an outlier, the actual number of prescriptions is 129 and the expected number of prescriptions is 14; (iii) for Painkiller C, which is not flagged as an outlier, the actual number of prescriptions is 50 and the expected number of prescriptions is 52. In this example, because Painkiller B is flagged as an outlier, scorecard 402 provides a text summary identifying it as such.

It should be noted that a purpose of scorecard 402 is to communicate outlier prescription activity to the Doctor in order to encourage the Doctor to change his/her behavior. As such, it may not always make sense to simply provide the Doctor with a prescription likelihood score, as the prescription likelihood score may not be the most effective way to communicate outlier behavior. Instead, as shown in FIG. 4, in many embodiments scorecard 402 communicates outlier behavior by other means, such as by comparing expected behavior to actual behavior. In these embodiments, the score itself might not necessarily be used in the communication to the subscriber. However, scorecard 402 is just one example of a way of representing outliers, and many other known (and yet to be known) methods of representing outliers (and calculating scores) may be used. Furthermore, although scorecard 402 is depicted in the present embodiment as being included in an electronic mail message, other embodiments may use other methods for presentation and/or delivery of the scorecard. For example, in some embodiments, scorecard 402 is delivered via alternative electronic formats, such as via SMS message or via a web-based document delivery and/or posting system. In other embodiments, scorecard 402 is delivered in a physical (that is, non-electronic) fashion, such as via a paper letter delivered by postal mail.

III. FURTHER COMMENTS AND/OR EMBODIMENTS

Some embodiments of the present invention recognize the following facts, potential problems and/or potential areas for improvement with respect to the current state of the art: (i) the amount of fraud and abuse in healthcare and healthcare insurance is often difficult to detect and prosecute with minimal impact on legitimate medical services; (ii) there is an absence of normative and outcomes-based approaches for managing the costs of healthcare incidents and episodes based on prevailing best practices; (iii) existing fraud metrics do not account for normalizations that might influence the metric at the individual encounter level (for example, the severity of the health conditions of a particular patient); (iv) existing methods yield a large number of false positive fraud detections; and/or (v) existing methods do not automatically learn a connection between a diagnosis/procedure and a prescription of a class of drugs (and instead, for example, rely on pre-specified rules and/or arbitrary connections).

Some embodiments of the present invention may include one, or more, of the following features, characteristics and/or advantages: (i) utilizing statistical modeling methods in fraud and abuse analytics; (ii) identifying potential investigation targets for fraud and abuse in health care claims; (iii) identifying new and/or unknown patterns of fraud; (iv) reducing fraud supported by falsified claims; (v) controlling health care costs; (vi) reducing prescription-drug related crimes; (vii) identifying potential fraud from unstructured/unlabeled data; and/or (viii) using a graphical model with latent variables to connect disparate data sources to investigate fraud and abuse.

Embodiments of the present invention provide an approach for detecting fraud and abuse in healthcare claims, inspired by ideas from computer speech recognition and language modeling. More specifically, the approach in these embodiments predicts the prescription outcomes during a treatment encounter from the historical profiles of the participating entities. By analogy, the elements of the historical profiles are treated similarly to "words" in a speech vocabulary, which are comprised into "sentences" using language models and smoothing techniques. The probable prescription behavior is then recognized from the "sentence" context.

In many embodiments of the present invention, the joint probability of a prescribed drug, combined with relevant patient and prescriber profiles, is represented as a directed graphical model. The graphical model contains latent variables to connect entities in prescription claims to the appropriate diagnosis code and procedure code profiles in related medical claims, when possible. Many of these embodiments use smoothing techniques to obtain robust joint probability estimates, and further, many embodiments use interpolation techniques to address the limitations in independence assumptions of the variables in the graphical model. The resulting graphical model representation can efficiently compute the probability that a certain prescriber exceeds a certain number of prescriptions for a target drug and accordingly issue an audit recommendation.

Embodiments of the present invention connect medical insurance claims and prescription drug-related insurance claims to identify potential fraud and/or abuse. In one example, embodiments of the present invention can distinguish a doctor specializing in palliative care (that is, pain mitigation) who prescribes a large amount of pain killers from a pediatrician who also prescribes a large (and likely excessive) amount of pain killers. In another example, embodiments of the present invention can flag a doctor who has large (and possibly excessive) numbers of patient visits while lacking a corresponding prescription trail.

Once potential fraud and/or abuse has been detected, embodiments of the present invention provide feedback for behavior modification to reduce cumulative abuse. In one example, an audit investigator can compare expected prescription levels and observed levels, as well as flag individual patients and/or prescriptions with fraud scores. In many embodiments, scorecards are provided to prescribers/providers to indicate potential fraud and allow prescribers/providers the ability to adjust their practices accordingly.

Embodiments of the present invention are also adapted to include interpretable models that provide insight into the origin of fraud and/or abuse. For example, graphical models may be adapted to learn complex relationships, down to the level of each prescriber/specialist's capabilities. Embodiments of the present invention are further adapted to model complex domains (such as healthcare) in terms of conditional independence relationships, utilizing, for example, probabilistic expert systems, graphical models, and/or Bayesian networks.

Figure 5:
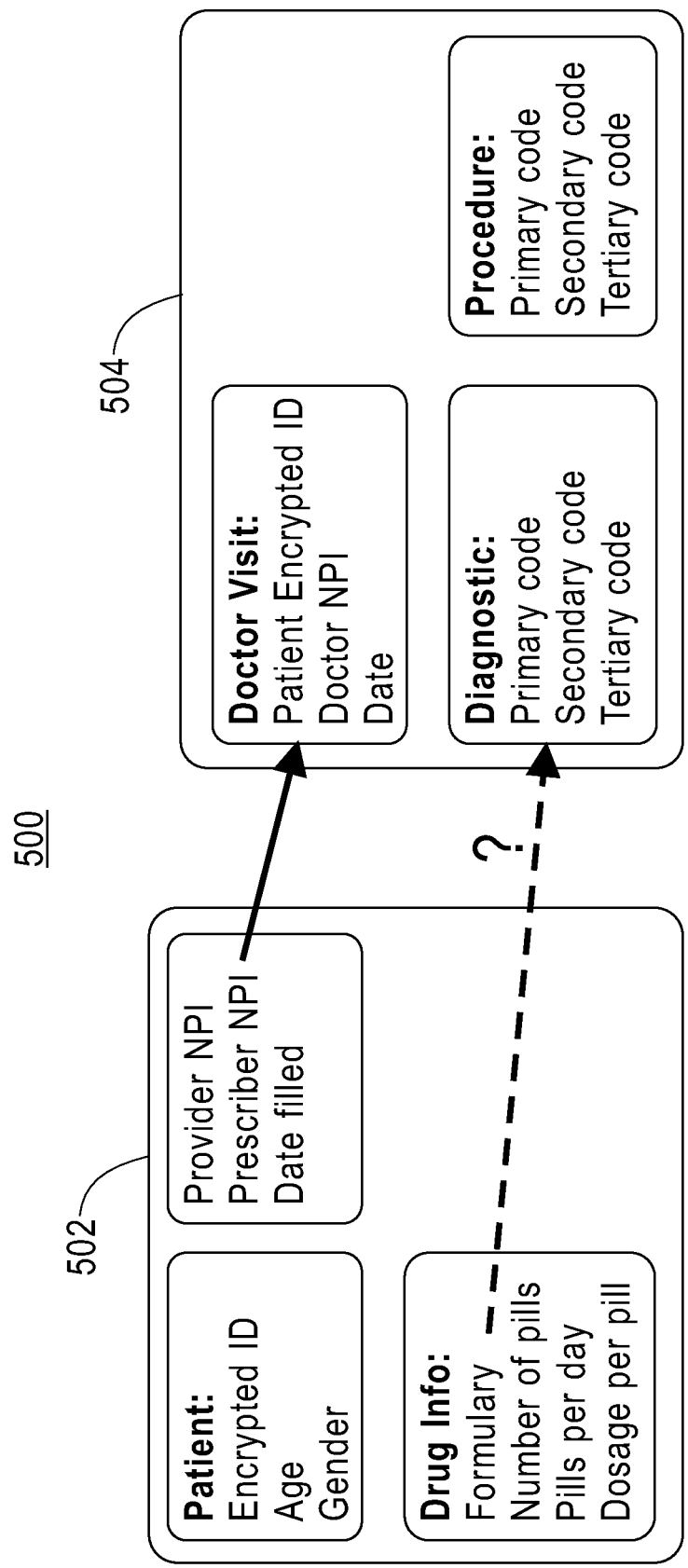
FIG. 5 is a diagram showing information that is helpful in understanding data that is used by a second embodiment system according to the present invention.

Some embodiments of the present invention identify fraud and/or abuse in healthcare claims data using statistical detection methods. For example, in some embodiments, two separate databases—one for issued prescriptions (called a "prescription database") and one for medical diagnoses (called a "medical claims database")—are provided. In some of these embodiments, diagnoses (or medical procedures) from the medical claims database are not directly linked to specific prescriptions in the prescription database. However, other information included in the respective databases may be used to draw correlations between diagnoses and prescriptions. For example, a diagnosis for a patient by a doctor may be similar to other diagnoses made by the doctor for the patient, or may be similar to other diagnoses made by the doctor for other patients. Embodiments of the present invention look at such patterns of inclusion to extract a probabilistic link modeled using latent variables in a graphical model. FIG. 5 includes diagram 500, depicting prescription database 502, medical claims database 504, and their corresponding relationships according to some of these embodiments.

Some embodiments of the present invention utilize a graphical model with latent variables to link diagnoses codes with prescriptions and improve the prediction of prescribed drugs. In one example, a doctor has provided 20 diagnosis codes and has performed 3 medical procedures for a specific patient. By using a graphical model, networked computers system 100 is able to verify the viability of prescriptions the doctor writes for the patient. This occurs even when the dates of prescriptions do not directly correlate to the dates of diagnoses and/or medical procedures. In another example, a doctor prescribes a pain medication to a patient without issuing any diagnosis codes (and without a prior history of issuing diagnosis codes for the patient). This particular problem can occur when a diagnosis relating to the prescription was issued a long time ago—long enough that it is no longer contained in medical claims database 504. By using graphical model 500, system 100 is able to use other diagnosis codes issued by the doctor for other patients to assess the reasonableness of the prescription.

In many embodiments of the present invention, prescription database 502 and medical claims database 504 come from different sources. For example, medical claims database 504 may come from an employer-based medical plan provider, while the prescription database 502 may come from an employer-based prescription drug provider.

Some embodiments of the present invention provide a prescriber scorecard for each prescriber (that is, a person who writes prescriptions, such as a doctor). In these embodiments, the prescriber scorecard highlights prescriber behavior in the different therapeutic drug classes for which the prescriber has written prescriptions (scores on the scorecard may be computed relative to the predictions from graphical model 500, for example). More specifically, in these embodiments, prescription data is accumulated for a particular prescriber/provider (such as a doctor/pharmacy) to detect outlier behavior. Known algorithms such as the Viterbi algorithm may be used to detect outliers. When new outlier behavior is detected, system 100 may utilize behavior modification techniques to encourage the prescriber/provider to analyze their behavior. For example, in some embodiments, the prescriber/provider is notified of the outlier behavior and provided with a report indicating expected behavior versus actual behavior over time. In other embodiments, prescriber scorecards include peer-normalized prescribing behavior comparing the prescriber's behavior to that of his or her peers.

Figure 6:
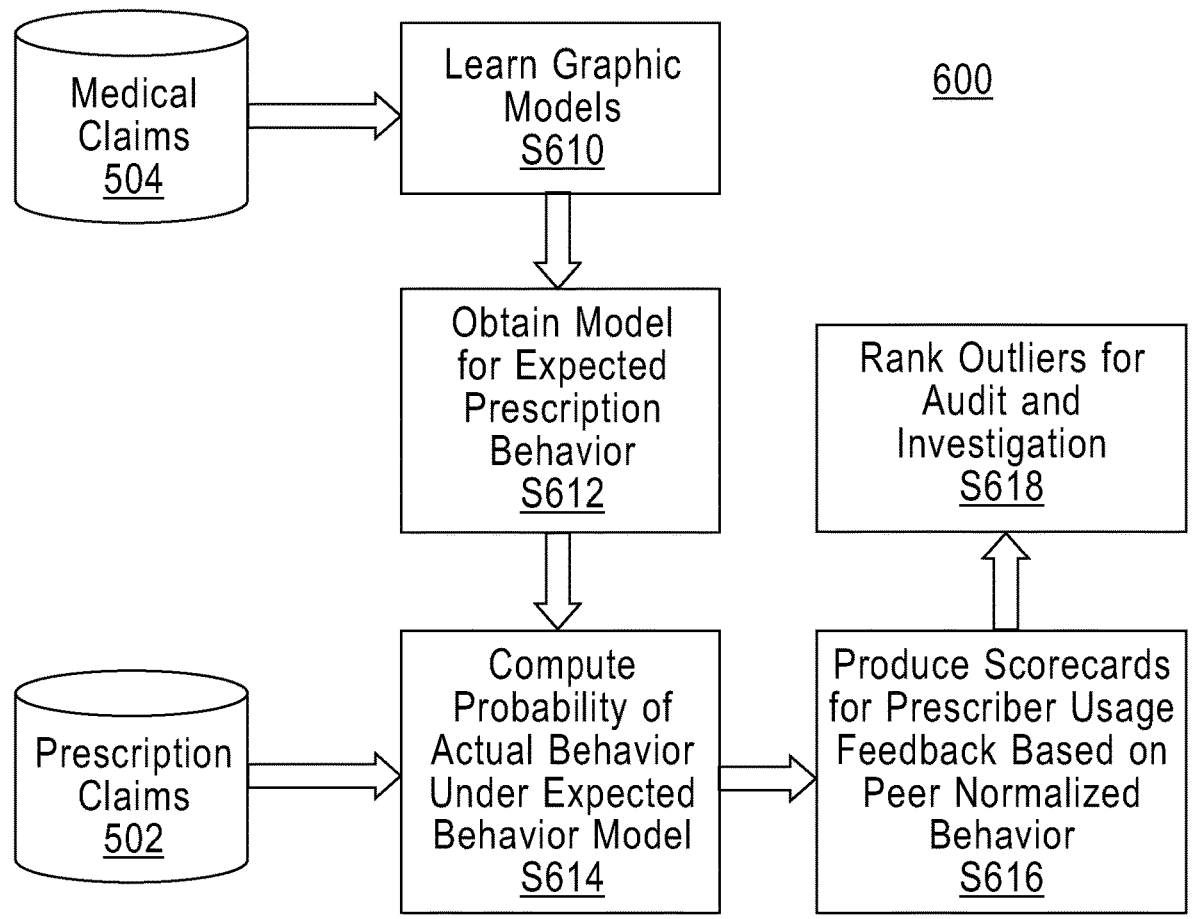
FIG. 6 is a flowchart showing a second embodiment method performed, at least in part, by the second embodiment system.

FIG. 6 shows flowchart 600 depicting a method according to the present invention. Processing begins at step S610, where system 100 uses medical claims from medical claims database 504 (see FIG. 5) to train a joint model by using an appropriate factorization/graphical model. In this embodiment, the model is represented as P(drug, age, gender, diagnosis code, doctor specialty, procedure code). It should be noted that in this embodiment, the variables in the model are all discrete, but the number of probability states is rather large due the variety of drugs and the fact that diagnosis codes and procedure codes can be multi-valued. As such, other non-important (from a fraud and abuse standpoint) variables relating to specific drug codes (such as, for example, packaging and/or brand names) have been disregarded (that is, not included) in order to reduce dimensionality.

Processing proceeds to step S612, where system 100 obtains a model for expected prescriptions. In one embodiment, Bayes' rule is used to create this model, which is represented as P(drug|age, gender, diagnosis code, doctor specialty, procedure-code).

Processing proceeds to step S614, where system 100 uses prescription claims from prescription database 502 to compare actual, observed prescriptions to the expected prescription model. Or, stated another way, in this step, system 100 computes the probability of the actual (observed) behavior under the expected behavior model. In this embodiments, expected prescription amounts are represented as E[#prescriptions of drug|patient, diagnosis information]. The expected prescription amounts are compared to the observed prescriptions, and an outlier score represented as P[#prescriptions>=observed amount|patient, diagnosis information] is computed. In this step, both the expected prescription amounts and the outlier scores are calculated across all prescriptions of a prescriber (or provider) using the probabilities computed in step S612 as well as using dynamic programming algorithms such as the Viterbi algorithm (to be discussed in further detail, below).

Processing proceeds to step S616, where scorecards are created for each prescriber (or provider) based on the probabilities computed in step S614. The scorecards describe the actual behavior of prescribers/providers relative to the normative model computed in step S612. Additionally, in many embodiments, the probabilities are normalized based on peer behavior.

Processing proceeds to step S618, where outliers in the observed prescriptions (as viewed on the scorecards) are identified and ranked for potential audit and further investigation. In a cost-management framework, the identified and ranked prescriptions can be further used by claims originators for additional behavior modification (to be discussed in further detail, below).

The following paragraphs will now discuss a second example embodiment according to the present invention. Generally speaking, discussion of this embodiment will include a description of graphical models used for fraud detection, with a focus on prescribers who are responsible for prescription claims for a given formulary class. As used herein in this sub-section, any discussion of the "present embodiment," the "example embodiment," or the like is meant to refer to this second example embodiment, as opposed to the (first) example embodiment discussed in the previous sub-section of this Detailed Description.

As discussed above in relation to FIG. 6 (and specifically, steps S610 and S612), a target of the present invention is to create a contingency table that models expected behavior for combinations of prescriptions, diagnoses, and medical procedures. Table 1, below, shows the amount of data in prescription database 502 and medical claims database 504 used to create the contingency table for the present example embodiment:

TABLE 1

| Prescription Database | | Medical Claims Database | |
|---|---|---|---|
| Prescriptions | 53,106,279 | Visits | 105,215,113 |
| Patients | 3,514,249 | Patients | 1,994,866 |
| Doctors | 125,208 | Doctors | 106,764 |
| Pharmacies | 4,623 | Diagnostic codes | 18,500 |
| Formularies | 21,279 | Procedure codes | 14,664 |

As such, the size of the corresponding contingency table will be $1.26 \times 10^{15}$ entries, which can be calculated by multiplying the following numbers together: (i) the number of formularies/drugs (21,279); (ii) the number of diagnostic codes (18,500); (iii) the number of procedure codes (14,664); (iv) the number of different patient ages (109—not shown in Table 1); and (v) the number of genders (2—not shown in Table 2).

In discussion of the present example embodiment, for simplicity purposes, certain variables (such as, for example, formularies/formulary classes, patients, and/or doctors) will be represented by symbols. Table 2, below, depicts the various symbols that may be used to refer to these variables in this sub-section. Additionally, as used herein, the capital letter "P" represents a probability, and the character "|" represents the term "given" (for example, P(a|b) is interpreted as the probability of "a" given "b".

TABLE 2

| Variable | Symbol | Domain |
|---|---|---|
| Formulary/Formulary Class | r | R |
| Diagnostic Code | d | D |
| Procedure Code | p | Π |
| Age | a | A |
| Gender | g | G |
| Specialty/Profession Code | s | S |

As discussed above, one way to reduce dimensionality of graphical models of the present invention is to combine or remove non-important variables. Another way to reduce dimensionality is to impose some restrictions on the graphical model structure. For example, Formula 1, below, represents a factorization of the joint probability distribution according to the present example embodiment.

$$P(r,a,g,d,p,s) = P(r)P(a,g|r)P(s|r)P(d|r)P(p|r) \qquad \text{Formula 1}$$

Figure 7A:
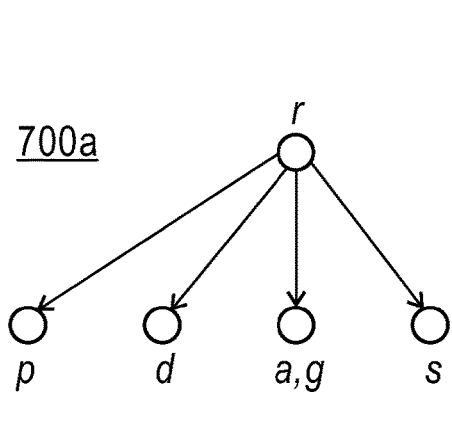
FIG. 7A is a diagram showing a visual representation of a graphical model generated by the second embodiment system.

The factorization in Formula 1, which greatly reduces the model dimension, is further represented in directed graphical model 700a (see FIG. 7A). Referring to FIG. 7A, the variables that are not directly connected in graph 700a are conditionally independent given the other variables. Model 700a describes the joint probability of an outcome in a given prescription class resulting from a specific encounter in which the patient's age and gender, the prescriber's specialty, and the resulting diagnosis and procedure codes are conditionally independent. The probabilities in model 700a can be obtained from the individual co-occurrence counts of each variable. For example, P(a,g|r) can be estimated as $N(r,a,g)/\Sigma_{a,g}N(r,a,g)$, where N(r,a,g) is the number of prescriptions of drug therapeutic class r for patients of age a and gender g.

Figure 7B:
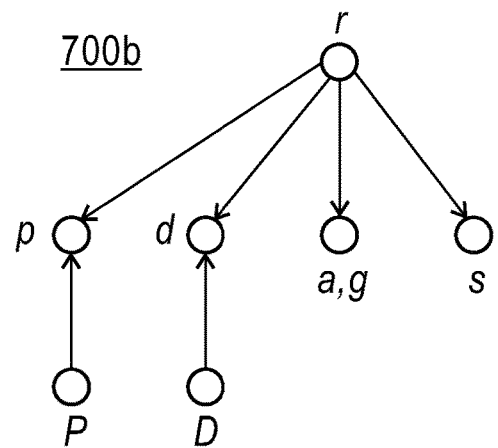
FIG. 7B is a diagram showing a visual representation of a graphical model generated by the second embodiment system.

Because prescriptions in prescription database 502 are not directly linked to diagnoses and procedures in medical claims database 504, a different factorization, corresponding to a different graphical model, must be used. Graphical model 700b (see FIG. 7B) depicts p and d as hidden observations, where p is a prescription with the set of possible prescriptions and d is a diagnosis within the set of possible diagnoses. Formula 2, below, is a formula representing graphical model 700b (see FIG. 7B).

$$P(r, a, g, s, D, \Pi) = P(r)P(a, g \mid r)P(s \mid r) \times \left(\sum_{d \in D} P(d \mid r)P(d \mid D)\right)P(D) \times \left(\sum_{p \in P} P(p \mid r)P(d \mid \Pi)\right)P(\Pi) \qquad \text{Formula 2}$$

In Formula 2, a number of the variables come from observed values. In the present example embodiment, the probabilities for these observed values are calculated as follows (where "N" represents the total number of prescriptions, "n(s,r)" represents the number of prescriptions where a doctor with a specialty s is prescribing formulary r, and "n(r)" represents the number of prescriptions for formulary r):

$$P(s, r) = \frac{n(s, r)}{N} \qquad \text{Formula 3}$$

$$P(r) = \frac{n(r)}{N} \qquad \text{Formula 4}$$

$$P(s \mid r) = \frac{P(s, r)}{P(r)} = \frac{n(s, r)}{n(r)} \qquad \text{Formula 5}$$

Regarding the remaining, unobserved (or hidden) variables, estimations must be made for their respective probabilities. In the present example, probabilities for hidden variables are computed using the following formulas (where gamma ("γ") is a "soft-count" estimate of how often a diagnosis occurs given that a particular drug was prescribed at time t, and omega ("ω") is the time-invariant version of gamma):

$$\omega_{d \mid r} = \sum_{t: r_t = r, d \in D_t} \gamma_t(d \mid r) \qquad \text{Formula 6}$$

$$\gamma_t(d \mid r_t) = \frac{P_{k-1}(d \mid r_t) P(d \mid D_t)}{\sum_{d' \in D_t} P_{k-1}(d' \mid r_t) P(d \mid D_t)} \qquad \text{Formula 7}$$

$$P_k(d \mid r) = \frac{\omega_{d \mid r}}{\sum_{d' \in D} \omega_{d' \mid r}} \qquad \text{Formula 8}$$

In the present embodiment, to generate a model for expected prescriptions (see discussion of step S612, above) the 21,279 known formularies are grouped into 97 groups (known as "therapy classes"). Therapy classes are used by prescribers and pharmacists to classify drugs according to their medical function, and the drugs in each therapeutic class tend to treat the same set of medical conditions. Examples of therapy classes include, but are not limited to: (i) narcotic analgesics, which relieve pain; (ii) antibiotics, which kill bacterial infections; and (iii) anticonvulsants, which prevent seizures. In the present example embodiment, all 97 therapy classes are used to train the joint probability model. However, in other embodiments, other combinations may be used (and models may subsequently be specialized to individual therapy classes).

A common measure of goodness in language modeling (and a measure used in the present example embodiment to create a prescription model) is the perplexity. As referred to in the present example embodiment, perplexity is the geometric average of possible therapy classes given the available prescription context. Perplexity is used in the present example to evaluate the models generated in step S610 (discussed above). Formula 9, below, is an example of a formula for performing this evaluation, where "PP" is the model's perplexity, "e" is the mathematical constant "e", "LL" is the conditional log likelihood with respect to therapy classes, and p and d are as described above.

$$PP = e^{-LL_{pd}} \qquad \text{Formula 9}$$

Table 3, below, depicts the values of LL and PP for the present example embodiment. More specifically, Table 3 shows the perplexity for some basic model factorizations that do not use the variables d or p.

TABLE 3

| | Model | | | |
| --- | --- | --- | --- | --- |
| | Train | | Test | |
| Joint Model | LL | PP | LL | PP |
| uniform | −4.57 | 97 | −4.57 | 97 |
| P(r) | −3.70 | 40.6 | −3.70 | 40.6 |
| P(r, a, g, s) | −3.43 | 30.9 | −3.45 | 31.4 |

As shown in Table 3, there is no significant difference in the perplexity on the test data and the training data for the uniform model and P(r). However, for the more sophisticated model P(r,a,g,s) (which is factorized to P(a,g|r)P(s|r) P(r)), there is a gap between the training and test performance. As shown in the table, two third of drug classes are eliminated as choices by using age, gender, specialty, and the relative frequencies of the therapy classes.

In order to determine links between prescriptions and possible diagnoses, linkage sets (that is, sets of possible diagnoses) are created. Linkage sets (also referred to as "connection types" and/or "connection sets") are used experimentally to narrow down possible diagnoses. It should be noted that the more constrained the linkage set, the sharper the model that can be trained. However, smaller sets have less data to train the models P(d|r) and P(p|r), and as such increase the likelihood of overtraining the model. Ultimately, the amount of constraint used in creating linkage sets should be balanced with the amount of available training data. The linkage sets used in the present example embodiment are shown in Table 4.

TABLE 4

| Linkage Set | Description |
| --- | --- |
| D | All visits to the prescribing doctor are considered. |
| P | All the visits to the prescribing doctor by the patient are considered. |
| T | Same as P, but only including visits earlier in time than when the prescription was filled. |
| V | Same as P, but only including visits occurring on the same day the prescription was filled. |
| 1 | Only primary diagnostic codes and primary procedure codes are used. |
| 3 | As in 1, but secondary and tertiary diagnostic and procedure codes are also used. |

Because linkage sets vary from patient to patient, the graphical model may be able to learn the underlying prescription-diagnosis link. In one example, three patients are prescribed painkillers: (i) Patient 1 has had diagnoses of back pain and high blood pressure; (ii) Patient 2 has had diagnoses of a tooth ache and back pain; and (iii) Patient 3 has had diagnoses of malaria and back pain. From this example, it is reasonable to suspect a strong connection between back pain and the prescription of a painkiller. Furthermore, more examples may also demonstrate that the link between high blood pressure and painkiller prescriptions is low.

Table 5, below, depicts the sizes (measured in millions of prescriptions) of some of the linkage sets discussed above for the present example embodiment. For example purposes, the "train" data (or "training data") includes the first six months of prescriptions in a given year, and the "test" data includes prescriptions in the third quarter of that same year. For each linkage set, 3 columns are included: (i) one for model d: P(r|a,g,s,D); (ii) one for model p: P(r|a,g,s,Π); and (iii) one for model d+p: P(r|a,g,s,D,Π).

TABLE 5

| Connection | Evaluation Set | | | | | |
|---|---|---|---|---|---|---|
| | Train | | | Test | | |
| | d | p | d and p | d | p | d and p |
| All | | 31.4 | | | 15.4 | |
| D | 28.3 | 28.5 | 28.2 | 13.9 | 14.0 | 13.8 |
| P | 9.39 | 9.34 | 9.23 | 4.81 | 4.72 | 4.67 |
| T | 8.22 | 8.18 | 8.07 | 4.58 | 4.49 | 4.44 |
| V | 4.06 | 4.11 | 4.03 | 2.32 | 2.31 | 2.27 |

The following observations can be made from the data in Table 5: (i) at the level of the doctor, the linkage sets cover 90% of all available data; (ii) almost half of all the prescriptions are filled on the same day as a patient saw a specific doctor, when the patient doctor pair had entries in medical claims database 504; and (iii) only about ⅓ of the prescriptions had corresponding data for a doctor visit by the same patient.

As demonstrated above, in the present example embodiment, for much of the available data, there is no corresponding latent variable connection, even at the doctor level. Formula 10 depicts an example of a simple model where no latent variables are used. Formula 10 is an example of a back-off model, which is a type of smoothing model (which will be discussed in further detail, below).

$$P(r, a, g, s, D) = \begin{cases} P_1(r, a, g, s)P(d \mid r) & \text{if } D \neq 0 \\ P_2(r, a, g, s) & \text{if } D = 0 \end{cases} \quad \text{Formula 10}$$

Figure 8A:
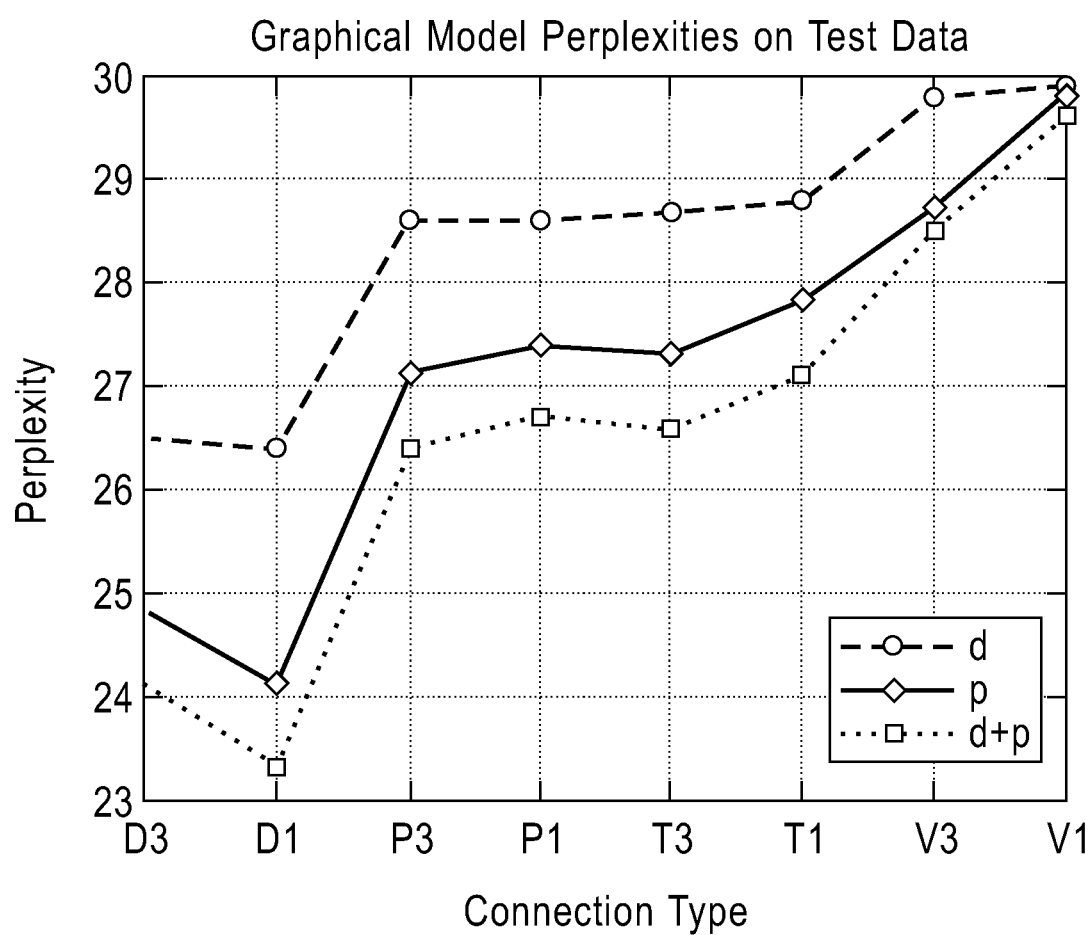
FIG. 8A is a graph showing information that is helpful in understanding the second embodiment system.

Chart 810 (see FIG. 8A) depicts the accuracy of selected models on the test data used in the present example embodiment. More specifically, chart 810 depicts the perplexity for models d, p, and d+p for each linkage set/connection type. As can be seen in chart 810, the best model is $P(r,a,g,s,D_{D1})$, and using procedure information H or sharper linkage sets than D1 gives higher perplexities.

Figure 8B:
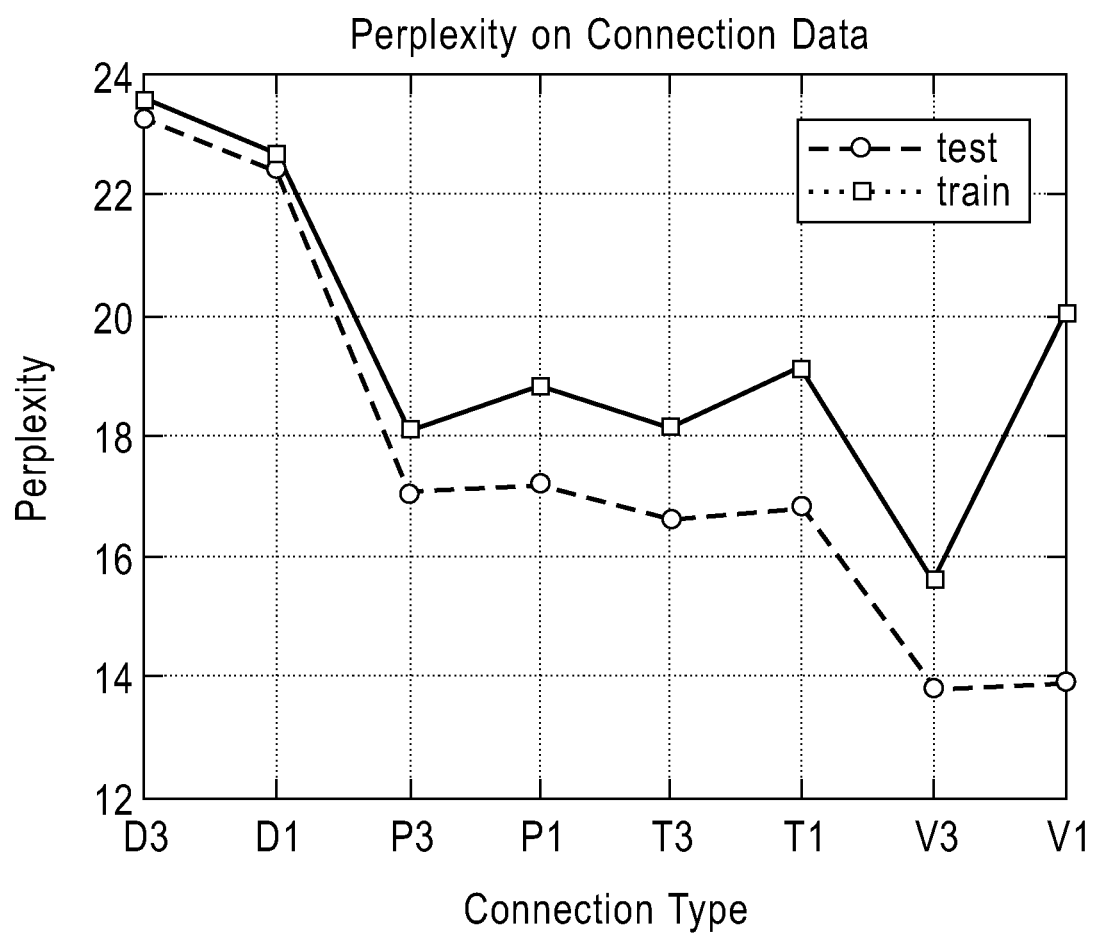
FIG. 8B is a graph showing information that is helpful in understanding the second embodiment system.

Chart 820 (see FIG. 8B) depicts the perplexity only on the data where the corresponding linkage set is empty, D≠0. As shown in FIG. 8B, using secondary and tertiary codes is generally better at all levels with the exception of at the doctor level, where there was no data shortage. The lowest perplexity on the test set is 15.6 at level V3, which is a substantial improvement over the best number, 23.3, in FIG. 7A. Chart 820 also shows that the gap between test and training perplexity increases when the linkage sets decrease in size. This is a sign that models may have been overtrained and that smoothing (discussed further, below) may be beneficial.

Table 6, below, depicts crossover perplexities according to the present example embodiment. More specifically, Table 6 depicts the perplexity values for crossover models, where, for example, the D1/D3 entry represents the perplexity on the test data with D1 entries where a model has been trained on training data with D3 entries. In Table 6, the bolded values represent the best model choices for each of the target test time models.

TABLE 6

| | Train Type | | | | | | | |
|---|---|---|---|---|---|---|---|---|
| Test | D3 | D1 | P3 | P1 | T3 | T1 | V3 | V1 |
| D3 | 23.5 | 23.4 | 24.5 | 24.2 | 24.6 | 24.6 | 25.4 | 24.9 |
| D1 | 22.9 | 22.6 | 24.2 | 24.0 | 24.4 | 24.3 | 25.3 | 26.0 |
| P3 | 20.7 | 20.4 | 18.5 | 18.7 | 18.6 | 18.7 | 20.0 | 20.8 |
| P1 | 22.1 | 21.6 | 19.6 | 19.2 | 20.0 | 19.9 | 24.0 | 26.2 |
| T3 | 20.6 | 20.3 | 18.4 | 18.5 | 18.4 | 18.5 | 19.9 | 20.6 |
| T1 | 22.2 | 21.7 | 19.7 | 19.2 | 19.8 | 19.7 | 23.6 | 26.0 |
| V3 | 18.1 | 17.9 | 15.6 | 15.7 | 15.6 | 15.7 | 16.0 | 16.4 |
| V1 | 20.4 | 20.1 | 17.5 | 16.6 | 17.7 | 17.8 | 18.4 | 20.3 |

As shown in Table 6, for each linkage set/connection type, there is at least one outlier value that breaks an otherwise clean model. As such, in the present embodiment, smoothing methods are used to reduce the effect of the outliers. In one example, a convex averaging smoothing method is used, where method 500 combines and/or averages different linkage sets. An example of this type of smoothing is depicted in Table 7, below. It should be noted that the example depicted in Table 7 utilizes similar—but not identical—data to the example depicted in Table 6.

TABLE 7

| Model | Test | Perplexity |
|---|---|---|
| V3 | V3 | 15.6 |
| T3 | V3 | 15.3 |
| (T3 + V3)/2 | V3 | 15.10 |
| (5V3 + V3)/6 | V3 | 15.12 |
| (V3 + 5T3)/6 | V3 | 15.25 |
| (50V3 + 20T3 + D3)/71 | V3 | 15.05 |
| (P3 + D1)/2 | P3 | 18.34 |
| (P3 + 5D1)/6 | P3 | 18.97 |
| (5P3 + D1)/6 | P3 | 18.06 |

Back-off smoothing is another smoothing method used in the present embodiment. In back-off smoothing, smoothing occurs by use of connection back-off, an example of which is shown in Formula 11, below. In Formula 11, the model "backs off" if it does not find a connection to the next model at a given level, until it finally gives up and uses P(r,a,g,s). Table 8, below, depicts the result of using Formula 11 on the data in the present example embodiment. As shown in Table 8, one model is used at the visit level, one model is used at the patient level, and one model is used at the doctor level.

$$P(r, a, g, s, D) = \begin{cases} P(r, a, g, s, D_{V3}) & \text{if } D_{P3} \neq 0 \\ P(r, a, g, s, D_{P3}) & \text{if } D_{V3} \neq 0 \text{ and } D_{P3} \neq 0 \\ P(r, a, g, s, D_{D1}) & \text{if } D_{V3} = D_{P3} = 0 \text{ and } D_{D1} \neq 0 \end{cases} \quad \text{Formula 11}$$

TABLE 8

| V3-Model | P3-Model | D1-Model | Perplexity |
|---|---|---|---|
| V3 | P3 | D1 | 22.19 |
| (50V3 + 20T3 + D3)/71 | (5P3 + D1)/6 | D1 | 21.98 |

Referring still to the present example embodiment, once smoothing is complete, the resulting models are then interpolated. Because some models—for example, P(r,a,g,s) and P(r,a,g,s,d,p,D,Π)—operate in different domains, they cannot be directly averaged together. Instead, the first model is "lifted" into the parameter space of the second model, perhaps by making a new model—P(r,a,g,s)P(D)P(Π)—by using an independence assumption. However, the independence assumption may lead to a poor joint-distribution, and it is also not clear what the probabilities P(D) and P(Π) should be. As such, a conditional averaged model is used to learn interpolation weights by maximizing the likelihood on held-out data. Formula 12, below, is an example of a conditional averaged model according to the present embodiment. Formula 13, below, is an example of a formula for estimating the respective weights in Formula 12 using an Expectation Maximization (EM) algorithm.

$$P(r \mid a, g, s, D, \Pi) = \sum_{i=1}^{N} w_i P_i(r \mid a, g, s, D, \Pi) \quad \text{Formula 12}$$

$$w_i^{k+1} = \sum_{t=1}^{T} \frac{w_i^k P_i(r_t \mid a_t, g_t, s_t, D_t, \Pi_t)}{\sum_{j=1}^{N} w_j^k P_j(r_t \mid a_t, g_t, s_t, D_t, \Pi_t)} \quad \text{Formula 13}$$

In the present example embodiment, the models P(r,a,g,s,D), P(r,a,g,s,Π) and P(r,a,g,s,D,Π) are interpolated with different choices of weights. The weights were trained by using EM on held-out data (specifically, data pertaining to the fourth quarter of the previously discussed year). Table 9 shows the results of the interpolation (using the best back-off model from Table 8) with three different weight sets chosen by hand and one weight set trained by using EM on held-out data.

TABLE 9

| $w_d$ | $w_p$ | $w_{dp}$ | Perplexity |
|---|---|---|---|
| 1/2 | 1/6 | 1/3 | 21.364 |
| 1/3 | 1/3 | 1/3 | 21.483 |
| 4/5 | 1/5 | 0 | 21.444 |
| 0.604 | 0.211 | 0.185 | 21.357 |

Once the models have been interpolated and an expected prescription model has been obtained (see discussion of steps S610 and S612, above), the expected prescription model is then compared to actual behavior (see discussion of step S614, above). In many embodiments, this comparison takes place at a doctor level to identify whether a particular doctor is prescribing too much of a particular drug or class of drugs. In the present example embodiment, this comparison takes three steps: (i) computing P(r|context(t)) for prescription t for all therapy classes r and all t; (ii) computing the observed number of prescriptions, n(r)=#{t:r t=r}, for the target therapy class r; and (iii) computing the probability P(n>n(r)) by using a dynamic programming approach (which, in the present embodiment, is the Viterbi algorithm). Formula 14 demonstrates the Viterbi algorithm as used in the present embodiment (where arithmetic is performed in log-domain for numerical stability).

$P(n(t+1)==n \mid \text{context})=$ $P(r \mid \text{context}(t)) \times P(n(t)==n-1 \mid \text{context}(t)) + P(\text{not } r \mid \text{context}(t)) \times P(n(t)==n \mid \text{context})$    Formula 14

In some embodiments of the present invention, scorecards (such as those discussed in relation to step S616, above) are created for each prescriber/provider, depicting the differences between actual prescriber/provider activity and expected prescriber activity. Table 10 depicts an example of a possible prescriber scorecard. In Table 10: (i) the "Amt." column represents the number of actual prescriptions; (ii) the "Exp." Column represents the number of expected prescriptions; (iii) the ">99% Q" column represents the interval the prescriber should fall in at least 99% of the time, according to the expected prescription model; and (iv) the "Score" column represents the Viterbi score, where large scores (such as the bolded score) represent outliers.

TABLE 10

| Description | Amt. | Exp. | >99% Q | Score |
|---|---|---|---|---|
| Amphetamine prep. | 4 | 3.1 | [0, 8] | −1.0 |
| Analgesics. narcotic | 189 | 2.8 | [0, 7] | −674.0 |
| Antiarthritics | 2 | 0.5 | [0, 3] | −2.6 |
| Anticonvulsants | 25 | 44 | [0, 59] | 0 |
| Antihistamines | 1 | 3.0 | [0, 8] | −0.1 |
| Antiparkinson | 14 | 7.0 | [0, 14] | −4.5 |
| Ataractics-tranqui. | 73 | 131.3 | [0, 153] | 0 |
| Laxatives | 1 | 0.4 | [0, 2] | −1.0 |
| Psychostimulants | 88 | 166.6 | [0, 189] | 0 |

In some embodiments of the present invention, the expected prescription model can compute not only the probability of over-prescription, but also other quantities useful in interpreting fraud candidates. Once the model has found potential fraud candidates, the candidates may be used in a number of ways. For example, the fraud candidates may be used to alert doctors of over-prescription behavior compared to what is expected from the doctors' corresponding prescription and patient profiles.

Although the present example embodiment utilizes minimal temporal contextual information, in some embodiments of the present invention, additional temporal information—such as patients' continued use of particular drugs—may be included. In these embodiments, additional temporal information may be modeled using, for example, a Markov chain or a Hidden Markov Model (or "HMM").

Some embodiments of the present invention may include one, or more, of the following features, characteristics and/or advantages: (i) a method for identifying entities in a claims database for potential audit due to abnormal behavior, such as fraud and abuse, and providing behavior modification feedback using data that cannot explicitly be linked; (ii) a means to accumulate evidence from individual prescriptions across a doctor's entire prescription portfolio using dynamic programming (such as the Viterbi algorithm); (iii) a method to connect disparate information such as medical claims and prescription claims (for example, using diagnosis and procedure codes to inform prescription behavior); (iv) a means to bring in medical claims at the patient or doctor level to refine prescription information beyond basic patient and doctor demographics by use of latent/hidden graphical model variables and an EM algorithm; and/or (v) providing auxiliary information for deep-dive analysis of top-ranked entities for investigation and prosecution.

Furthermore, some embodiments of the present invention may include one, or more, of the following additional features, characteristics and/or advantages: (i) sending prescription over-usage notices to doctors—comparing their usage to expected usage; (ii) the potential to significantly reduce drug overconsumption; and/or (iii) providing a detailed understanding of relations between diagnoses, procedures, and prescriptions that would normally require multiple medical experts.

IV. DEFINITIONS

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein are believed to potentially be new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

Module/Sub-Module: any set of hardware, firmware and/or software that operatively works to do some kind of function, without regard to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, application-specific integrated circuit (ASIC) based devices.

What is claimed is:

1. A computer-implemented method comprising:
   receiving, by one or more computer processors, a set of observed data including (i) prescription data from a first database, and (ii) patient care event data from a second database;
   estimating, by one or more computer processors, a set of latent variables from the set of observed data using an expectation maximization method;
   generating, by one or more computer processors, a set of graphical models utilizing the set of observed data and the set of latent variables, the set of graphical models including at least: (i) a first graphical model that models relationships between prescription values of the first database and diagnosis values of the second database, and (ii) a second graphical model that models relationships between the prescription values of the first database and procedure values of the second database;
   interpolating, by one or more computer processors, at least the first graphical model and the second graphical model to generate an expected prescriptions model; and
   utilizing, by one or more computer processors, the expected prescriptions model to verify viability of a set of prescriptions written by a provider, the set of prescriptions including at least: (i) a first prescription having a date that does not directly correlate to a date of a diagnosis or a date of a procedure in the set of patient care event data, and (ii) a second prescription that does not directly correlate to any diagnoses in the set of patient care event data.

2. The computer-implemented method of claim 1, further comprising computing, by one or more computer processors, expected prescriptions for a new set of patient care event data using the expected prescriptions model.

3. The computer-implemented method of claim 2, further comprising identifying, by one or more computer processors, outlier prescription behavior in a new set of prescription data based, at least in part, on the expected prescriptions computed using the expected prescriptions model.

4. The computer-implemented method of claim 3, wherein identifying the outlier prescription behavior further comprises:
   computing, by one or more computer processors, using one or more dynamic programming algorithms, a probability that an actual number of prescriptions, from the new set of prescription data, having prescription values of a certain class would exceed an expected number of prescriptions, from the computed expected prescriptions, having prescription values of the certain class.

5. The computer-implemented method of claim 3, further comprising, in response to identifying the outlier prescription behavior, triggering, by one or more computer processors, an audit process to investigate for insurance fraud.

6. The computer-implemented method of claim 5, wherein the second database is a medical claims database from a health insurance provider.

7. The computer-implemented method of claim 3, further comprising:
   in response to identifying the outlier prescription behavior, generating, by one or more computer processors, a report indicating expected prescription behavior compared to actual prescription behavior for a particular prescriber; and
   providing, by one or more computer processors, the report to the particular prescriber.

8. The computer-implemented method of claim 7, further comprising normalizing, by one or more computer processors, the expected prescription behavior compared to the actual prescription behavior in the report according to peer prescription behavior.

9. The computer-implemented method of claim 7, wherein the report flags outlier prescription activity for the particular prescriber.

10. The computer-implemented method of claim 1, wherein:
    the first graphical model further models relationships between the prescription values of the first database and diagnosis value profiles of the second database, the diagnosis value profiles including diagnosis values as well as patient profiles and prescriber profiles; and
    the second graphical model further models relationships between the prescription values of the first database and procedure value profiles of the second database, the procedure value profiles including procedure values as well as the patient profiles and the prescriber profiles.

11. A computer program product comprising one or more computer readable storage media and program instructions collectively stored on the one or more computer readable storage media, the stored program instructions executable by one or more processors, the stored program instructions comprising:
    program instructions to receive a set of observed data including (i) prescription data from a first database, and (ii) patient care event data from a second database;
    program instructions to estimate a set of latent variables from the set of observed data using an expectation maximization method;
    program instructions to generate a set of graphical models utilizing the set of observed data and the set of latent variables, the set of graphical models including at least: (i) a first graphical model that models relationships between prescription values of the first database and diagnosis values of the second database, and (ii) a second graphical model that models relationships between the prescription values of the first database and procedure values of the second database;

program instructions to interpolate at least the first graphical model and the second graphical model to generate an expected prescriptions model; and program instructions to utilize the expected prescriptions model to verify viability of a set of prescriptions written by a provider, the set of prescriptions including at least: (i) a first prescription having a date that does not directly correlate to a date of a diagnosis or a date of a procedure in the set of patient care event data, and (ii) a second prescription that does not directly correlate to any diagnoses in the set of patient care event data.

12. The computer program product of claim 11, the stored program instructions further comprising program instructions to compute expected prescriptions for a new set of patient care event data using the expected prescriptions model.

13. The computer program product of claim 12, the stored program instructions further comprising program instructions to identify outlier prescription behavior in a new set of prescription data based, at least in part, on the expected prescriptions computed using the expected prescriptions model.

14. The computer program product of claim 13, wherein the program instructions to identify the outlier prescription behavior further comprise:

program instructions to compute, using one or more dynamic programming algorithms, a probability that an actual number of prescriptions, from the new set of prescription data, having prescription values of a certain class would exceed an expected number of prescriptions, from the computed expected prescriptions, having prescription values of the certain class.

15. The computer program product of claim 13, the stored program instructions further comprising program instructions to, in response to identifying the outlier prescription behavior, trigger an audit process to investigate for insurance fraud.

16. A computer system comprising a processor set and a computer readable storage medium, wherein:

the processor set is structured, located, connected and/or programmed to run program instructions stored on the computer readable storage medium; and the stored program instructions include:

program instructions to receive a set of observed data including (i) prescription data from a first database, and (ii) patient care event data from a second database;

program instructions to estimate a set of latent variables from the set of observed data using an expectation maximization method;

program instructions to generate a set of graphical models utilizing the set of observed data and the set of latent variables, the set of graphical models including at least: (i) a first graphical model that models relationships between prescription values of the first database and diagnosis values of the second database, and (ii) a second graphical model that models relationships between the prescription values of the first database and procedure values of the second database;

program instructions to interpolate at least the first graphical model and the second graphical model to generate an expected prescriptions model; and program instructions to utilize the expected prescriptions model to verify viability of a set of prescriptions written by a provider, the set of prescriptions including at least: (i) a first prescription having a date that does not directly correlate to a date of a diagnosis or a date of a procedure in the set of patient care event data, and (ii) a second prescription that does not directly correlate to any diagnoses in the set of patient care event data.

17. The computer system of claim 16, the stored program instructions further comprising program instructions to compute expected prescriptions for a new set of patient care event data using the expected prescriptions model.

18. The computer system of claim 17, the stored program instructions further comprising program instructions to identify outlier prescription behavior in a new set of prescription data based, at least in part, on the expected prescriptions computed using the expected prescriptions model.

19. The computer system of claim 18, wherein the program instructions to identify the outlier prescription behavior further comprise:

program instructions to compute, using one or more dynamic programming algorithms, a probability that an actual number of prescriptions, from the new set of prescription data, having prescription values of a certain class would exceed an expected number of prescriptions, from the computed expected prescriptions, having prescription values of the certain class.

20. The computer system of claim 18, the stored program instructions further comprising program instructions to, in response to identifying the outlier prescription behavior, trigger an audit process to investigate for insurance fraud.

* * * * *